United States Patent [19]

Zeng et al.

[11] Patent Number: 5,593,822
[45] Date of Patent: Jan. 14, 1997

[54] IGG DEPLETED SERUM PREPARATIONS AND METHODS FOR ANTIBODY PRODUCTION

[75] Inventors: Qing S. Zeng, Alhambra; Reiko F. Irie, Los Angeles, both of Calif.

[73] Assignee: John Wayne Cancer Institute, Santa Monica, Calif.

[21] Appl. No.: 163,186

[22] Filed: Dec. 7, 1993

[51] Int. Cl.⁶ .............................. A01N 1/02; C12P 21/04; C12N 5/00

[52] U.S. Cl. .................... 435/2; 435/70.1; 435/70.2; 435/70.21; 435/240.2; 435/240.26; 435/240.27; 435/240.3

[58] Field of Search ........................... 435/240.2, 240.21, 435/240.26, 240.27, 240.3, 2, 70.1, 70.2, 70.21, 170; 424/529, 531

[56] References Cited

U.S. PATENT DOCUMENTS

| | | | |
|---|---|---|---|
| 4,704,366 | 11/1987 | Juarez-Salinas et al. | 436/501 |
| 4,714,556 | 12/1987 | Ambrus et al. | 210/638 |
| 5,273,884 | 12/1993 | Gale et al. | 435/7.1 |

OTHER PUBLICATIONS

Wyatt et al, Adv. Anim. Cell. Biol. Technol. Bioprocesses (270–72) 1989.

Fujimoto et al., American Biotechnology Laboratory, 9(2) p. 54 (Mar. 1991).

Advanced Protein Products, Trends in Biotechnology, 5 (7) p. 187 (Jul. 1987) (see abstract).

Hy Clone, *Product & Services Guide for the Cell Culture Scientists* p. 6–13 (1993).

Savelkoul et al., J. of Immunological Methods, vol. 172, pp. 33–42 (1994).

Cole, S. P. C. et al., "Anitbody Production by Human Hybridomas in Serum–Free Medium," *J. of Immunol. Methods*, 78:271–278 (1985).

Darby, C. R., et al., "Purification of monoclonal antibodies from tissue culture medium depleted of IgG," *J. Immunol. Methods*, 159:125–129 (1993).

Glassy, M. C., et al., "Serum–Free Media in Hybridoma Culture and Monoclonal Antibody Production," *Biotech. and Bioeng.*, 32:1015–1028 (1988).

Heath, C., et al., "Methods for increasing monoclonal anitbody production in suspension and entrapped cell cultures: biochemical and flow cytometric analysis as a function of medium serum content," *J. Biotechnol.*, 15:71–90 (1990).

Jiskoot, W., et al., "Two–step purification of a murine monoclonal antibody intended for therapeutic application in man," *J. Immunol. Methods*, 124:143–156 (1989).

MacLeod, A. J. et al., "Use of Plasma Protein Fractions as Serum Substitutes for In Vitro Cell Culture," *Develop. Biol. Standard.*, 60:55–61 (1985).

Mariani, E., et al., "Commercial serum–free media: hybridoma growth and monoclonal antibody production," *J. Immunol. Methods*, 145:175–183 (1991).

Patel, T. P., et al., "Different culture methods lead to differences in glycoslation of a murine IgG monoclonal antibody," *Biochem. J.*, 285:839–845 (1992).

Schneider, Y–J., "Optimisation of hybridoma cell growth and monoclonal antibody secretion in a chemically defined, serum–and protein– free culture medium," *J. Immunol. Methods*, 116:65–77 (1989).

*Trends in Biotechnology*, 5(7):187, Jul., 1987.

*Primary Examiner*—Micheal G. Wityshyn
*Assistant Examiner*—Susan M. Dadio
*Attorney, Agent, or Firm*—Arnold, White & Durkee

[57] ABSTRACT

A method for preparing serum depleted of IgG to be used in the production of IgG monoclonal antibodies is disclosed. Animal serum is contacted with protein G or protein A prior to addition to base media to obtain a superior cell culture medium depleted of serum derived IgG antibodies. Included in the disclosure are improved media preparations for cell culture of antibody producing cells and incorporating the antibody depleted serum and improved methods of producing the antibodies.

34 Claims, 11 Drawing Sheets

1 2 3 4 5 6  8 9 10

1　2　　3　4

1   2   3   4   5       7   8

IGG DEPLETED SERUM PREPARATIONS AND METHODS FOR ANTIBODY PRODUCTION

The United States government owns rights in the subject matter of the present invention as research relevant to the development thereof was supported by grant numbers CA 56059, CA 30647 and CA 12582 from the National Institutes of Health.

BACKGROUND OF THE INVENTION

1. Field of the Invention

The present invention relates to the field of serum preparations for use in the in vitro production of IgG antibodies, and to methods for preparing serum depleted of intrinsic immunoglobulin. The invention also relates to the field of antibody preparation, including improved methods for the production of monoclonal antibodies in cell culture media.

2. Background of the Related Art

The use of pure monoclonal antibodies (MAb) both as therapeutic reagents in clinical practice and as immunological agents in biomedical research is growing steadily. Monoclonal antibodies are produced as an animal ascites fluid or from cell culture supernatants. The production of MAb in vitro by hybridoma cells, B lymphoblasts, Ig transfectomas and myeloma cell lines has many advantages over the use of animal ascites, which may contain both known and unknown viruses, natural antibodies, and other potentially hazardous substances.

These antibody producing cells (Ab-cell lines), typically grow better in vitro in medium supplemented with whole animal serum. In fact, the majority of B cell hybridomas grown in tissue culture medium require or prefer the presence of added whole animal sera. Whole animal serum, i.e., serum that has not been processed to exclude immunoglobulins and/or other naturally occurring substances contains many as yet unidentified constituents that appear to be necessary for optimal cell growth.

One of the many drawbacks of in vitro growth of Ab-cell lines in cell culture media with whole serum is the high cost of isolating and purifying antibody from the spent culture media. For example, whole serum introduces a relatively large concentration of immunoglobulins, such as IgG, to the culture system. Therefore, IgG antibody preparations from spent media of IgG MAb producing cultures is relatively impure, as the majority of the IgG in such media is derived from the serum source, and not the Ab-cell line.

Conventionally, the method of production of MAb has been to grow the Ab-cell line in serum which contains serum derived antibodies. The spent serum is then contacted with protein G or protein A which separates the IgG antibodies in the medium from the other medium components. These IgG antibodies are then eluted from the protein G or protein A. However, the antibodies so derived are a mixture of Ab-cell line produced IgG and the serum derived IgG. The desired IgG antibodies are then separated from the serum derived IgG, usually by an affinity chromatography column that is specific for the desired IgG.

These procedures are laborious and can handle only relatively small volumes of media containing antibody. In addition, the preparation of commercially valuable quantities of monoclonal antibody requires the processing of large volumes of tissue culture supernatant because the concentration of MAb is low and the antibody represents only a small fraction of the immunoglobulin present (Jiskoot et al., 1991).

To bypass and simplify the media purification procedure, Ab-cell lines may also be cultured in media that does not include serum at all, or that includes a serum substitute. A number of serum substitutes have been developed (Barnes, overview, 1987; Schneider, 1989; Federspiel et al., 1991), some of which are commercially available (Mariani et al., 1991). γ-Globulins Reduced Newborn Calf Serum (Sigma, USA) and Nu-Serum (Collaborative Research, USA) are two such available serum substitutes. However, the γ-Globulins Reduced Newborn Calf Serum (Sigma, USA) was found by the present inventors to be incapable of maintaining the growth of certain Ab-cell lines, such as TVE-1 cells. It is contemplated by the present inventors that the Cohn fractionation process, in which ethanol is used to precipitate γ-globulins, destroys constituents of the serum that are important in the growth of TVE-1 cells, and potentially other cell lines. In addition, this particular serum substitute was found by the present inventors to contain unacceptable amounts of bovine IgG.

Nu-Serum (Collaborative Research, USA) is a second exemplary serum substitute, and includes a reduced amount of IgG. However, this preparation has been reported to contain 2.5% serum (Mariani et al., 1991), and has been found to contain significant amounts of bovine IgG.

Studies by the present inventors also demonstrate that TVE-1 cell growth in culture media with the Nu-Serum preparation is inferior to cell growth in non-IgG depleted FCS-containing media. TVE-1 cell growth and antibody production in media containing Nu-Serum has also been observed by the present inventors to be significantly inferior to that achieved in media containing the IgG depleted serum of the present invention.

An additional disadvantage of currently available serum-free medias and serum substitutes, such as the Nu-Serum and others described herein, is that they frequently require time consuming modification for use with particular cell lines (Glassy et al., review, 1988). Thus, media that contain serum remain the standard, and are currently preferred for the growth of most cell lines and hybridomas (Jayme and Blackman, 1985).

Currently available modified serum culture supplements and serum-free medias fail to meet existing needs in the industry for optimal growth of Ab-cell lines and cost effective production and isolation of commercially significant amounts of antibody from cell culture. While serum-free or serum modified media may offer some advantages (Barnes, 1987), their use has the disadvantages of reduced cell growth and the necessity for costly and time consuming purification techniques. Therefore, there still exists an immediate need for a media supplement that supports cell growth comparable to that observed in serum-containing media, without the necessity of extensive costly and time consuming purification of the IgG.

SUMMARY OF THE INVENTION

The present invention seeks to overcome these and other drawbacks inherent in the prior art by providing an improved serum preparation which, surprisingly retains the cell growth properties of whole serum supplemented media without the problems of expensive and time consuming separation of Ab-cell produced IgG and the serum derived IgG. The present invention also provides methods of growing animal cell cultures and producing monoclonal IgG antibodies on a commercial scale due to the simplified purification procedures made possible by the serum preparations of the present invention.

A particular embodiment of the present invention is a method of preparing animal serum that is substantially depleted of IgG. The method comprises contacting the animal serum with protein A or protein G to remove the serum IgG before using the serum to culture cell lines that produce IgG antibodies. After the growth of the Ab-cells in the improved media, the supernatant is again contacted with protein A or protein G to bind the IgG antibodies in the supernatant. The protein A or G bound to IgG is then easily removed by centrifugation, for example and the IgG is eluted by standard methods. The remarkable improvement is that the IgG so produced is essentially free of serum derived antibodies. Thus the expensive and time consuming step of affinity chromatography to separate the Ab-cell antibodies from the serum derived antibodies is not necessary.

The protein A or protein G is preferably fixed to a solid substrate and protein-substrate is suspended in a volume of serum and allowed to mix for a certain period of time. The protein A or G bind the IgG antibodies in the serum and then are separated from the serum. It is understood that other proteins or modifications of protein A or G that bind IgG in serum may also be used. For example, modified, truncated, fused or otherwise altered forms of protein A or G that may be used to treat serum would also fall within the spirit and the scope of the present claims.

For example, protein A or G might be altered by site directed mutagenesis using techniques well known in the art, to produce a protein with altered characteristics which would also function to bind IgG and remove it from serum. It is understood that such altered proteins, or any functionally equivalent proteins would also fall within the scope of the present claimed invention.

In a preferred embodiment of the present invention, the protein A or protein G is fixed to a solid substrate. The solid substrate may be, but is not limited to, acrylic beads, beaded agarose or Sepharose. Crosslinking of the protein to the solid substrate can be accomplished by cyanogen bromide, oxirane, p-nitrophenyl chloroformate activation or by any other suitable means. A particular preferred embodiment is protein G crosslinked to Sepharose 4B Fast Flow available from Sigma catalogue #P 3296. The animal serum to be treated may be, but is not limited to bovine, goat, horse, pig or human serum, and is preferably bovine serum and even more preferably fetal calf serum (FCS).

By contacting the serum with protein A or protein G is meant, typically suspending the solid substrate crosslinked to the protein A or protein G in the serum to be treated and, in one preferred embodiment, incubating the suspension with agitation for an appropriate time period. In an alternate embodiment, the contact can be made in the form of a column connected to a peristaltic pump, for example to enhance the flow rate of the serum past the solid support. The contact step may be repeated two, three, four or even more than four times with further depletion of antibodies from the serum at each step.

It is understood that serum substantially depleted of IgG is meant to refer to serum from which a portion of the antibodies have been removed. For example, typically animal serum may contain about 0.4 mg/ml IgG, and serum with the IgG substantially depleted would contain less than about 0.4 mg/ml, or preferably less than from about 100 µg/ml to about 1 µg/ml and even more preferably less than from about 0.4 µg/ml to about 0.01 µg/ml. The level of antibody remaining in the antibody depleted serum may be determined by measuring the protein concentration, by SDS-PAGE protein separation, followed by scanning of a Silver stained gel by laser densitometry or by protein immunoblot analysis.

Another embodiment of the present invention is a method of preparing IgG monoclonal antibody comprising preparing IgG depleted animal serum and adding said serum to an appropriate culture medium. In a preferred embodiment a serum such as fetal calf serum is added to a culture medium such as RPMI 1640 so that the preparation contains about 5% serum by volume and more preferably about 1–2% serum by volume. It is understood that different cell lines have different requirements for serum and medium and that this particular preparation is provided by way of example only, and is not limiting in any way. The culture requirements of various cell lines are known, or can be established without undue experimentation and are included within the scope of the present claimed invention so long as the serum to be used is substantially depleted of IgG.

Media of the above description is demonstrated in the present disclosure to provide cell growth comparable to that observed in cell cultures with whole serum additives, and contains the desired depletion of exogenous IgG in supernatants from these cultures for the expeditious retrieval of IgG monoclonal antibody. In this regard, the cell culture media containing IgG depleted serum has been found to be particularly useful in the growth, maintenance, and antibody production by Ab-cell lines that produce IgG. It is understood that any cell line which has been developed to produce monoclonal or polyclonal antibody can be used in the present method. The cells to be cultured are preferably hybridoma, B-lymphoblastoid cells, Ig gene transfectoma or myeloma cells and more preferably mouse myeloma cells. Most preferably the cells are hybridoma TVE-1 cells.

The immunoglobulin produced by this method may be collected by various means well known in the art. These methods include centrifugation, gel filtration and any other means of separating the antibody bound to a solid substrate from a liquid solution. For example, when the antibody is enriched by suspending the solid antibody-capturing substrate (Protein A or G) in the spent culture media, the solid substrate would be collected by centrifugation, the liquid portion discarded, and the antibodies released from the solid substrate. When the serum is prepared by column gel filtration, the antibody containing phase is collected from the bottom of the column.

In the most preferred embodiment of the present invention, the monoclonal antibody to be collected is an IgG antibody or an IgG subclass. However, it is understood that other antibody isotypes, for example IgM, IgD, IgE and IgA, (and their subclasses) could also be produced by the method of the present invention when agents are isolated that will bind these isotypes specifically in an analogous manner as protein A and protein G bind IgG. Therefore, this method of producing an antibody depleted serum preparation would have a more general application.

Another embodiment of the present invention is a serum preparation comprising an animal serum substantially depleted of antibody. The serum may be any animal serum which includes, but is not limited to bovine, goat, horse, pig or human serum. Preferably the serum is bovine serum and more preferably fetal calf serum. The substantially depleted serum will contain less antibody than the untreated serum. For example, the serum preparation will contain less than about 0.4 mg/ml IgG, or preferably less than about 100

μg/ml IgG or even less than about 1 μg/ml IgG. Most preferably the serum preparation will contain less than about 0.4 μg/ml IgG and even more preferably less than about 0.01 μg/ml IgG.

A certain embodiment of the present invention is a serum preparation substantially depleted of IgG obtainable by contacting a volume of the animal serum with protein A or protein G affixed to a solid substrate and collecting the animal serum. The serum is preferably fetal calf serum, and the solid substrate may be any convenient matrix, such as acrylic beads, agarose or Sepharose and more preferably the solid substrate is Sepharose 4B fast flow. In certain embodiments, the serum preparation is essentially free of endotoxin. By essentially free of endotoxin, it is understood that endotoxin is present at levels no greater than 0.06 EU/ml as measured by E-Toxate (Sigma, USA, catalogue #210-B1).

Another preferred embodiment of the present invention is a cell culture media for the culture of a myeloma or hybridoma cell line comprising a base culture media and less than about 10% of a serum supplement, the serum supplement having less than about 0.4 mg/ml IgG. In preferred embodiments, the serum supplement may include between about 100 and about 10 μg/ml IgG and more preferably the serum supplement would include less than 0.01 μg/ml IgG.

The serum to be used in the cell culture media could be any appropriate animal serum and is most preferably fetal calf serum. The cell line to be cultured is a hybridoma or a myeloma cell line and is preferably a mouse myeloma cell line and most preferably TVE-1. In this embodiment of the invention, the base culture media is preferably RPMI 1640. It is understood that the media may comprise other additives to enhance cell growth for particular cell lines.

The serum preparation of the invention that includes substantially reduced amounts of immunoglobulin IgG, is designated for the purpose of describing the present invention as "–G" serum. As used throughout the description of the present invention, the term –GFCS will also be interchangeably used with the term "IgG reduced," "IgG depleted" and "–G" in the description of the serum preparations.

The modified serum preparations of the present invention with reduced IgG are relatively stable, and therefore may be conveniently stored under appropriate conditions for future use without loss of efficacy in cell culture. For example, volumes of the reduced IgG serum preparations of the present invention may be stored at –4° C. for extended periods of time.

The present disclosure demonstrates that the –GFCS medium is effective in supporting cell growth, particularly myeloma cell growth. The ability of these media to support growth demonstrates that no essential constituents in the fetal calf serum were destroyed by the depletion of IgG. The use of recombinant protein G also allowed bovine albumin, a useful constituent, to remain in –GFCS.

The use of –GFCS made possible the culturing of cells without transferring them to another medium. This has important advantages: saving time, reducing the risks of contamination, and avoiding damage to cells caused by washing and centrifuging, normally up to 3 times. In addition, the harvesting time is reduced to 2 days, or about 1/3.5 of the time required by conventional methods (Hasting et al., 1992; Kanda et al., in press). Using –G the total antibody yield is increased by at least 15 fold over that produced by the previous method. This includes a 2.8 fold increase compared with AIM-V media, approximately a 2 fold increase by "cell-keeping" culture, and a 3.5 fold increase by the shortened period of culture.

DETAILED DESCRIPTION OF THE PREFERRED EMBODIMENT

Figure 1:
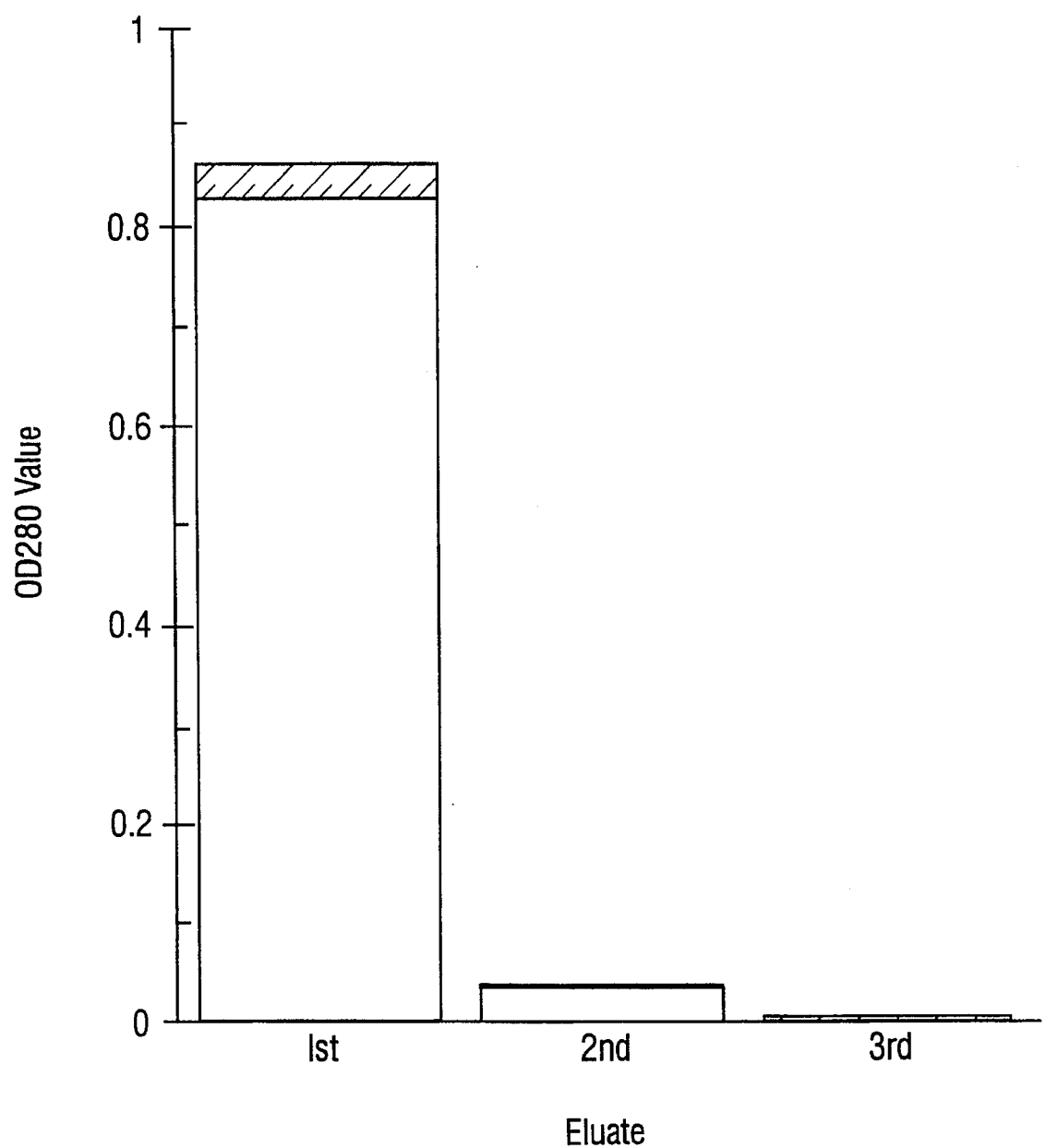
FIG. 1 $OD_{280}$ value of bovine IgG from the 1st, 2nd, and 3rd eluates. The volume of each eluate was 40 ml. Data were from 8 experiments: mean ±SE. 85 ml FCS was applied for each experiment.

The present invention provides new and important serum preparations and novel methods of growing antibody producing cell lines. The present invention also encompasses methods for using the serum preparations in highly efficient techniques for the in vitro production of IgG monoclonal antibodies. The serum preparations of the invention can be used to produce high yields of IgG monoclonal antibody surpassing the production yields of conventional serum supplemented media and without the time-consuming and costly purification steps typically involved in the isolation of antibody from spent media obtained with standard serum containing culture techniques.

The serum of the present invention is prepared so as to deplete and/or significantly reduce the concentrations of IgG in standard serum. Use of these serum preparations in vitro allows for an efficient and rapid technique for isolating commercially valuable quantities of highly purified preparations of IgG monoclonal antibodies suitable for clinical use at significantly reduced cost than has previously been possible.

The present studies surprisingly demonstrate that serum having reduced and/or depleted IgG in a culture media will support successful Ab-cell line growth and monoclonal antibody production comparable to media containing natural fetal calf serum, the gold standard against which media and serum media supplements and substitutes are judged. Thus, the disadvantages associated with the use of whole serum, such as the presence of high concentrations of IgG and its subclasses, are avoided without loss of growth and antibody producing activity. By simply depleting or reducing serum IgG prior to supplementing a cell culture media, the serum IgG contamination is essentially eliminated, and optimal hybridoma cell growth and monoclonal antibody production is preserved.

Protein G, a cell surface protein of Group G streptococci, is a type III $F_c$ receptor containing 2 or 3 binding domains that bind to the $F_c$ region of IgG by a non-immune mechanism (Bjorck and Kronvall, 1984; Boyle and Reis, review, 1987). Protein G, which has a broader range of binding than protein A, binds to polyclonal and/or monoclonal IgG from human, cow, mouse and other species (Akerstrom et al., 1985; Akerstrom and Bjork, 1986). The protein G gene has been sequenced (Fahnestock et al., 1986), and recombinant protein G has been produced in *E. coli* through genetic recombination techniques (Guss et al., 1986; Lew 1991). Recombinant protein G was designed to eliminate serum albumin binding while maintaining efficient binding to the $F_c$ region of IgG isotypes (Nygren et al., 1988), and can bind to human IgG at concentrations of over 20 mg per ml of gel when conjugated to a solid support matrix such as agarose.

TVE-1 Cell Line

TVE-1 was used as a model IgG-producing cell line, and was adapted to grow in RPMI 1640 medium containing 5% FCS. TVE-1 is P3X63.Ag8.653 mouse myeloma cell line transfected with a chimeric mouse $V_H$ and $V_L$ of 4C10 mouse hybridoma antibody (Yamamoto et al., 1990) and human $IgG_1$ constant region (Hastings et al., 1992). The chimeric antibody is specific for the GM3 ganglioside antigen. In addition to RPMI 1640, both serum-free media, γ-globulin-reduced new born calf serum (γ-reduced NCS, Sigma, USA) and γ-globulin reduced Nu-serum (Collaborative Research, USA) were used in the study of serum supplementation.

Cell Cultures

Typically, $2 \times 10^5$ cells in 5 ml of culture media were placed in T25 flasks and incubated in a $CO_2$ incubator (37° C./5% $CO_2$) for 3 days. The preferred culture medium comprises 5% –GFCS in RPMI 1640 media.

Statistical Analysis

Two-sided tests were used to compare results from –GFCS to results with other media.

Even though the invention has been described with a certain degree of particularity, it is evident that many alternatives, modifications, and variations will be apparent to those of skill in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

EXAMPLE 1

Preparation of IgG Depleted Serum

The present example is provided to demonstrate the utility of the invention for preparing IgG depleted media from a variety of serum species thereby providing immunoglobulin-depleted sera for use in cell culture. By way of example, fetal calf serum (FCS), which may be obtained from Gemini Bioproducts, USA, may be depleted of IgG according to one of the following two procedures.

PROCEDURE 1

One hundred milliliters FCS are added to 25 ml protein G SEPHAROSE 4 Fast Flow Column (Pharmacia, Sweden) and shaken gently over 2 days in a cold room at 4° C. The effluent is collected and transferred to another protein G column and shaken overnight. The column is allowed to stand for a short time until the protein G Sepharose beads settle and the serum preparation depleted of IgG (–G or –GFCS) is collected.

The IgG-free FCS (–GFCS) may be used as a culture medium supplement at 5% concentration in RPMI 1640 medium to grow the mouse myeloma cell line P3X63.Ag8.653, which secretes an $IgG_1$ mouse-human chimeric monoclonal antibody (TVE-1). Cell density, viability, doubling time, and antibody production are measured and used as indices to compare the efficacy of the –GFCS serum supplement with that of whole FCS medium, AIM-V (Gibco, USA) and other serum-free media.

PROCEDURE 2

FCS is applied to a protein G column that is connected to a peristaltic pump (Pharmacia, Sweden). The sample is recycled through a protein G column at a low speed (e.g., 40 ml/hr) overnight, collected and the procedure repeated once more. –GFCS is sterilized by passage through a 0.2 µm pore Nalgene Filterware (Nalge, USA). –GFCS may be used as a media supplement at a concentration of less than 10% in RPMI 1640 medium with L-glutamine (JRH Biosciences, USA). Most preferably, a concentration of the –GFCS of about 5% in RPMI is used.

Fetal calf serum depleted of IgG by one of the two procedures described above was used in the following examples.

EXAMPLE 2

Production of IgG Monoclonal Antibodies in Media Supplemented with IgG-depleted Serum or Media The present example is provided to demonstrate one particularly preferred method by which IgG monoclonal antibodies may be produced in a cell culture media supplemented with the serum preparations of the present invention.

TVE-1 hybridoma cells were cultured in a base cell culture media of RPMI 1640 medium that included about 5% of the serum preparation described in Example 1. The serum supplement as prepared by procedure 1 was found to provide comparable cell growth and monoclonal antibody production in vitro as media supplemented with the serum supplement prepared by procedure 2 of Example 1. IgG monoclonal antibodies were isolated from the spent media of the TVE-1 cell cultures after growth for three days.

About 40 ml of spent tissue culture media from 8 T25 flasks of each medium supplemented with about 5% of the IgG-depleted fetal calf serum was collected and concentrated by ammonium sulfate precipitation. The precipitate was redissolved in 2 ml of distilled water and placed in dialysis tubing with a molecular weight cut-off of 12,000–14,000 daltons (Spectrum, USA) and dialyzed against PBS with a total of three changes every 6 hours. After centrifugation at 10,000 g for 30 min, the supernatant was applied to a 5 ml protein A SEPHAROSE column (Pharmacia, Sweden) and shaken gently for 2 hr. IgG was eluted with 0.1M glycine, pH 2.8, and immediately neutralized with 1M Tris buffer, pH 8.8. The eluate was dialyzed against PBS as above, and then centrifuged at 100,000 g for 30 min. The supernatant was passed through a 0.2 µm pore filter and aliquoted to a final concentration of 0.5 mg/ml in PBS. The final product can be sterilized by filtration. However, it is advisable to perform each step in a laminar flow tissue culture hood.

Endotoxin contamination might constitute a problem for the production of antibody used in vivo. Theoretically, protein A isolated from staphylococci and protein G purified from streptococci should not be contaminated with endotoxin (a product of Gram negative bacilli) but recombinant protein G produced by E. coli may be. However, this caveat was addressed by demonstrating that endotoxin-free water passed through a fresh protein G or protein A column (Pharmacia) was contaminated with endotoxin at the level of 0.06 EU/ml, i.e., comparable to RPMI 1640 (JRH). Nevertheless, efforts should be made to avoid every possibility of contamination in each step of the procedure. Glassware should be washed with endotoxin-free water, autoclaved at 121° C., followed by 3 hr. in a 250° C. oven; plastic equipment, reagents, solutions and water should be endotoxin-free.

TVE-1 antibody from the spent tissue culture media was purified by 50% ammonium sulfate precipitation followed by Protein A affinity chromatography. An antibody preparation that was more than 99% pure was obtained as determined by SDS-PAGE, immunoblotting and protein concentration.

EXAMPLE 3

Characterization of IgG-depleted Media

The present example is provided to demonstrate the reduced IgG content of the IgG depleted serum preparations of the present invention. As used in the description of the present invention, the term "essentially IgG free" is used, and is defined as a concentration of 0.1% of residual IgG or less in the culture media in which the –GFCS is used as the serum additive.

SDS-PAGE Electrophoresis and Western Blot Analysis of Immunoglobulin-Depleted Media To test the depletion of IgG in –GFCS, 10 µl of –G was applied to a Western Blot immunoassay, and 10 µl unprocessed FCS was used as a positive control. Goat anti-bovine IgG or IgG (γ specific) (kpl, USA) and rabbit anti-goat IgG-POD (kpl, USA) were sequentially applied and the blot was developed using 4-chloro-1-naphthol. The purity of the final TVE-1 antibody product was tested by both SDS-PAGE electrophoresis and Western Blot analysis. In SDS-PAGE analysis, 20 µl samples of 0.1 mg/ml and 0.2 mg/ml were applied in non-reduced and reduced (β-mercaptoethanol) conditions and the protein bands were detected by staining with Coomasie Brilliant Blue R250. For Western Blot analysis, the concentration of TVE-1 was 0.4 mg/ml, and 10 µl/well were applied. Rabbit anti-FCS (DAKO, Denmark) and goat anti-rabbit POD (kpl, USA) were used sequentially. Reactive bands from test samples as well as from FCS of different concentrations were compared.

ELISA

Bovine IgG in purified TVE-1 IgG fractions was measured by ELISA. Purified bovine IgG (Sigma, USA) was used as a standard. Samples were diluted in carbonate buffer (pH 9.6), coated on ELISA plates and incubated for 90 min at room temperature. After blocking with human albumin for 90 min, goat anti-bovine IgG (kpl, USA) and rabbit anti-goat IgG-POD (kpl, USA) were sequentially applied. The ELISA was developed with o-phenylenediamine (OPD, Sigma, USA), and read by an ELISA reader (Molecular Device, USA) at 490 nm.

Depletion of IgG from FCS by Protein G Affinity Chromatography

The amount of bovine IgG in –GFCS was tested using three different assays, $OD_{280}$ value by spectrophotometer, Western Blot, and ELISA.

Ten milliliters –GFCS was applied to a 5 ml protein G column (the third application to the column) and incubated at 4° C. overnight. Protein was then eluted out of the column with 0.1M glycine, pH 2.8. The eluate was immediately neutralized with 1M Tris, pH 8.8, and the optical density (OD) measured with a spectrophotometer (LKB Biochrom, England) at a wavelength of 280 nm. An $OD_{280}$ of 1.350 is equivalent to 1 mg IgG. As shown in FIG. 1, the $OD_{280}$ of the eluate (10 ml) from the third depletion with the protein G column was around 0, compared with the $OD_{280}$ of the eluate after the first depletion, which was about 4.000, and after the second depletion, about 0.130.

Figure 2:
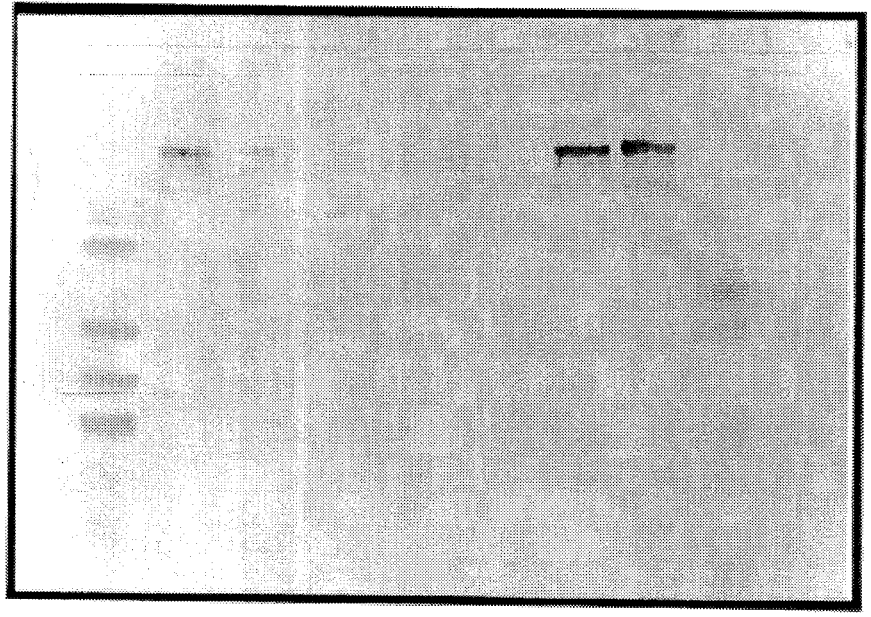
FIG. 2 Western Blot analysis of residual bovine IgG in –GFCS and in other media. –GFCS, 10 μl/well (lane 6). Control: FCS, 1:10, 100, 1,000, and 10,000 (lanes 2, 3, 4, 5 respectively); Nu-serum, 1:10 (lane 8); γ-globulin reduced NCS, 1:10 (lane 9). Lanes 1 and 10 were prestained standards for the low and high ranges, respectively. Goat anti-bovine IgG (1:800) and rabbit anti-goat POD (1:800) were used sequentially, and color was developed with 4-chloro-1-naphthol and $H_2O_2$.

As demonstrated by Western Blot analysis, no IgG band was detected in the –G lane, although a significant band was detected in the whole FCS lane at a 1:100 dilution, and a faint band is detected in the whole FCS lane at 1:1,000 dilution (FIG. 2). This result implies that residual bovine IgG in –G is less than that in a 1/1,000 dilution of FCS. Bovine IgG in FCS used in this study was measured as about 0.4 mg/ml. There are also strong bands in lanes of γ-globulin reduced NCS and Nu-serum. In an ELISA, the bovine IgG residue in –G was not more than 0.01 μg/ml (data not shown).

Contamination of Serum Proteins Derived from the Tissue Culture Media

TVE-1 IgG was purified by a two-step procedure, salt precipitation and protein A purification. The antibody preparation was analyzed and shown by SDS-PAGE electrophoresis and Western Blot immunoassay to contain less IgG than a 1/10,000 dilution of FCS. However, bovine IgG in the lane corresponding to the TVE-1 fraction was detectable. These bands are possibly due to cross-reaction between human and bovine IgG, which were detectable with the anti-FCS reagent bovine IgG throughout the preparation of –GFCS.

EXAMPLE 4

Endotoxin Analysis of –GFCS Depleted Media

The present study was performed to determine if the effluent of the Protein G column contains endotoxin. Endotoxin-free water was passed through the columns in the same manner as for –GFCS. The effluent was tested for endotoxin levels using the E-Toxate Kit.

Endotoxin Analysis

HiTrap protein G (1 ml) and protein A SEPHAROSE (1 ml) (Pharmacia, Sweden) were washed with 6 ml of endotoxin-free water; the seventh ml of water was collected as the sample. E-Toxate (Sigma, USA) prepared from the Limulus amebocyte lysate was used to detect endotoxin according to the manufacturer's instructions. RPMI 1640 (JRH, USA) was used as a control. The samples contained only an insignificant level of endotoxin (0.06 EU/ml), similar to RPMI 1640 (JRH).

EXAMPLE 5

Comparison of Cell Growth and Antibody Yield Between –G and Other Media

Figure 3A:
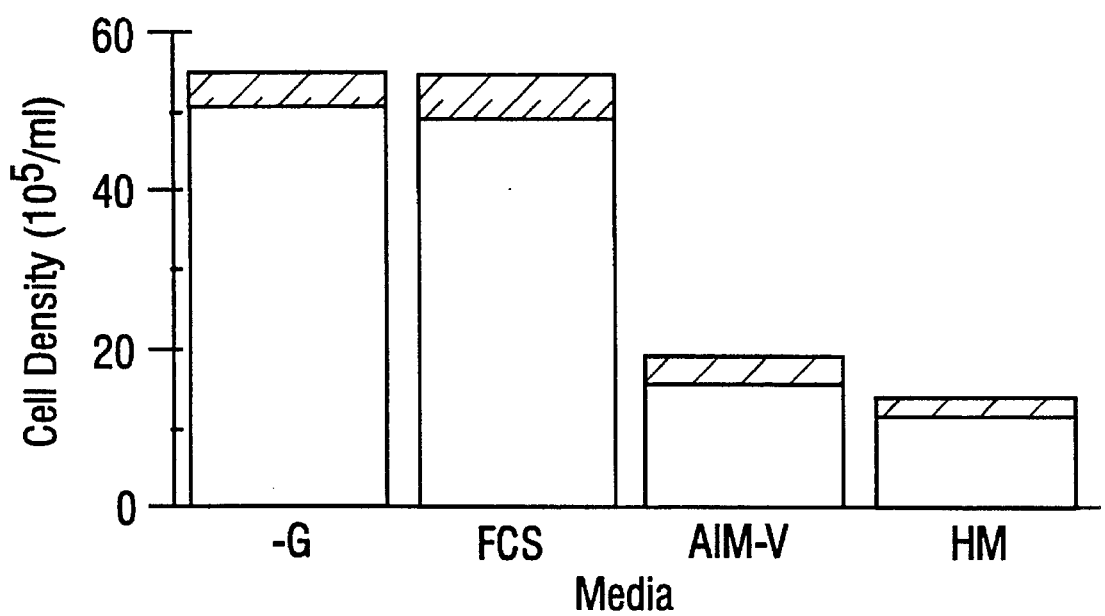
FIG. 3A Cell density comparison after growth of TVE-1 cells in various media. TVE cells, $2\times10^5/5$ ml were seeded to eight T25 flasks for each medium. After 3 days culture, the difference in cell density between –GFCS and FCS was not statistically significant (P=0.78), but the cell density in –GFCS media was significantly higher than that in AIM-V or in HM serum-free medium (P<0.001).
Figure 3B:
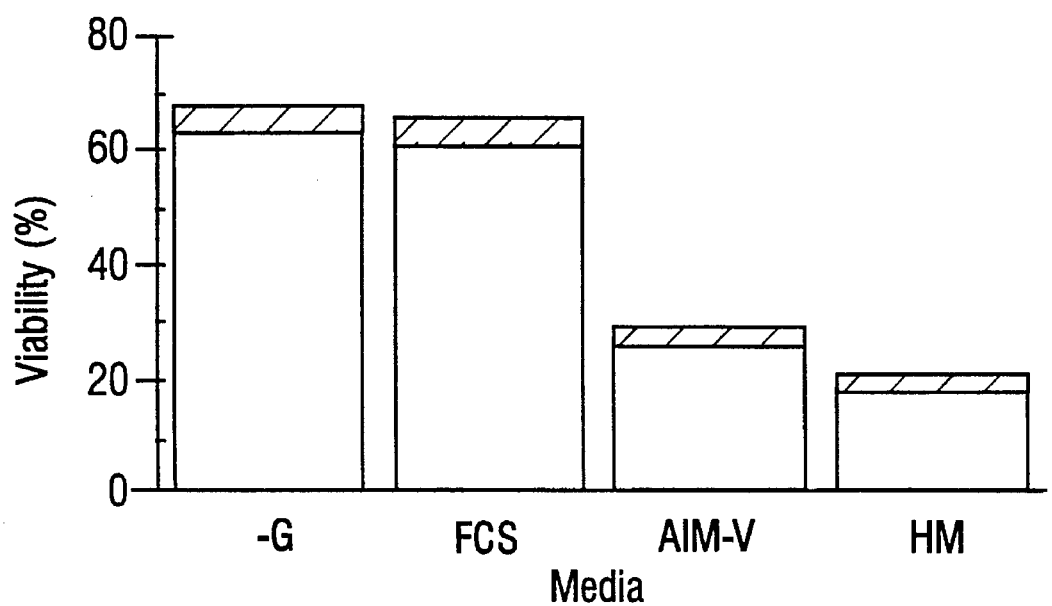
FIG. 3B Cell viability comparison after growth of TVE-1 cells in various media. The percentages of viability were determined by the 0.4% trypan blue exclusion test. The difference in cell viability between –GFCS and FCS was not significant (P=0.74), but the cell viability of –GFCS was much greater than that of AIM-V or HM (P<0.001).
Figure 3C:
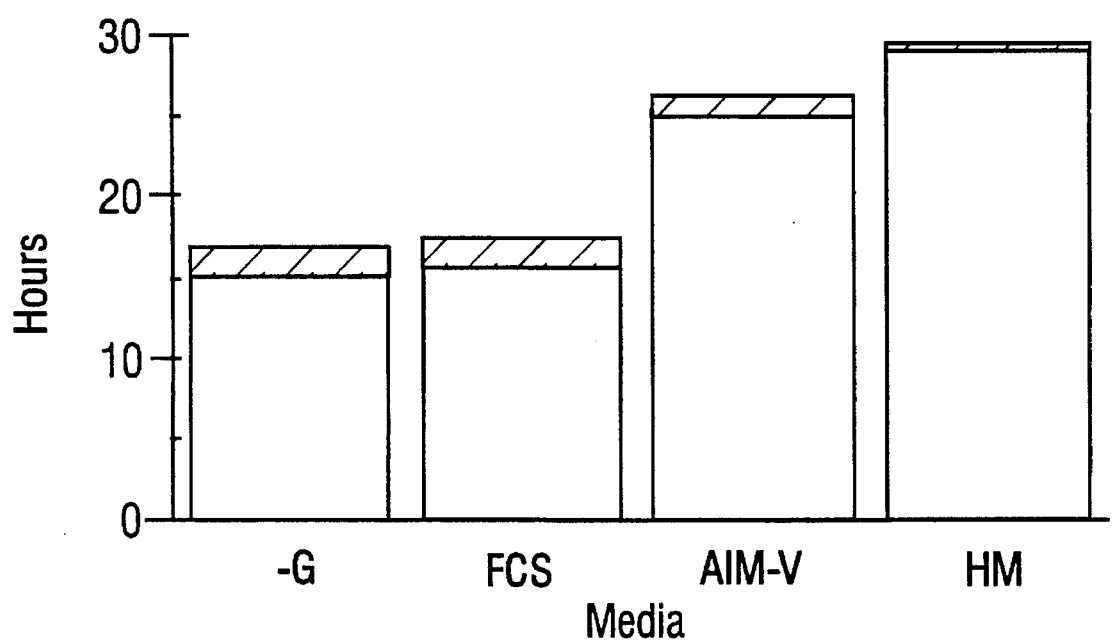
FIG. 3C Cell doubling time comparison after growth of TVE-1 in various media as in FIG. 3A. The doubling times were calculated by the formula stated in Example 5. The difference between the doubling times of cells in –GFCS and FCS was not statistically significant (P-0.79), but it was very significant between –GFCS and AIM-V or HM (P<0.001).

To determine the effect of antibody depletion from FCS, cell growth, viability and antibody yield were tested. Cell growth was analyzed after 3 days from cultures of $2\times10^5/5$ ml TVE-1 cells in –G, FCS, AIM-V and HM. Cell density (FIG. 3A), viability (FIG. 3B) and doubling time (FIG. 3C) were determined. Eight T25 flasks were tested for each medium. Cell viability was determined by 0.4% trypan blue exclusion and counted on a hemocytometer. Doubling time was calculated by the formula (Goding, 1986): $D.T.=0.693$ $t/\ln(n/n_0)$ [t=culture time, here 72 hr; $n_0$=starting cell count, here $2\times10^5$/ml; n=final cell counts from 8 flasks of different media].

Slight differences were noted in the cell density (p=0.78), viability (p=0.74), and doubling time (p=0.79) of –GFCS and FCS. Significant differences were observed, however, between –GFCS and both AIM-V and HM (p<0.001); cell density and viability were much higher, and the doubling time was shorter in both –GFCS and FCS supplemented media than in AIM-V or HM alone.

EXAMPLE 6

Comparison of TVE-1 IgG Antibody Production in –GFCS and Other Media

The present example is provided to demonstrate the utility of the present invention in the culture of monoclonal antibodies, and compares the MAb production achieved with the described serum preparation to other systems.

Figure 4A:
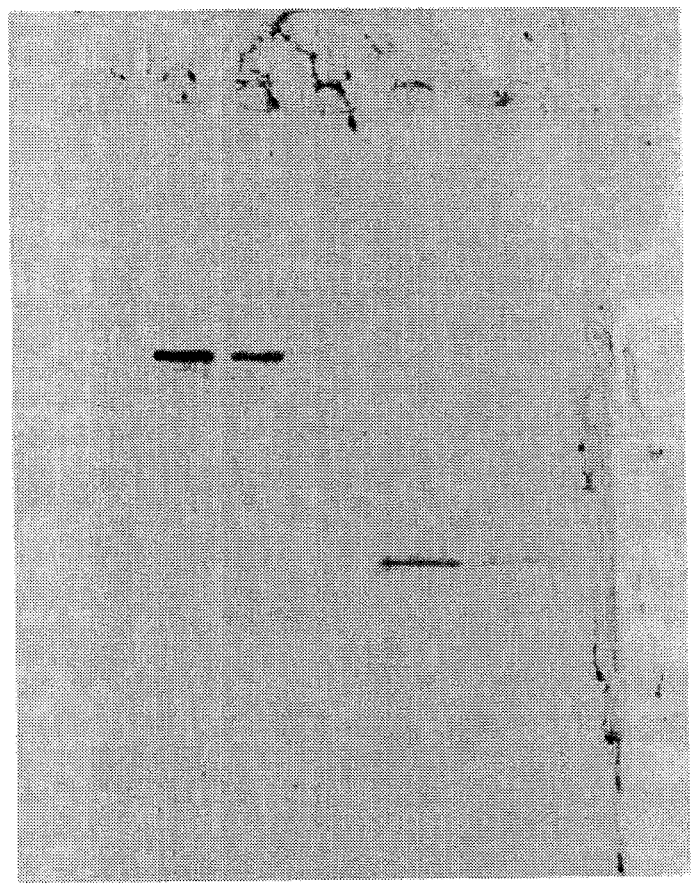
FIG. 4A SDS-PAGE analysis of purified TVE-1 chimeric IgG fraction. The purity of the product TVE-1 in 0.2 mg/ml (lanes 1,3) and 0.1 mg/ml (lanes 2,4) was tested by SDS-PAGE electrophoresis. Lanes 3 and 4 represent results from samples reduced with β-mercaptoethanol. The faint bands appearing beneath the major band are believed to comprise degraded IgG.
Figure 4B:
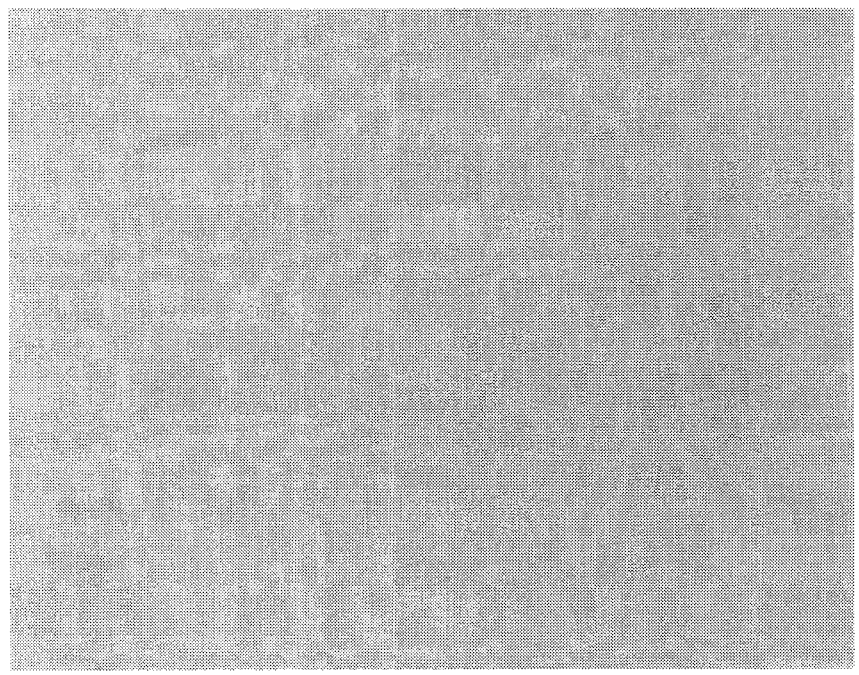
FIG. 4B Western Blot analysis of purified TVE-1 chimeric IgG fraction. TVE-1 (0.4 mg/ml, 10 μl/well) (lane 7) and control FCS at the following dilutions (1:100, 1:1,000, 1:10,000 and 1:100,000, 10 μl/well) (lanes 2,3,4,5 respectively) were analyzed by Western Blot. Lanes 1 and 8 are standards of the low and high ranges, respectively. Rabbit anti-FCS and goat anti-rabbit POD (1:800) were used sequentially and developed with 4-chloronaphthol and $H_2O_2$. The TVE-1 lane (lane 7) contains only the bands from IgG, which are believed to be a cross-reaction to anti-FCS, while the FCS lanes (even in a 1:10,000 dilution) contain faint bands corresponding to bovine albumin, indicating that possible contamination in TVE-1 is less than in FCS diluted 1:10,000.

Monoclonal IgG was isolated and purified from the –GFCS spent tissue culture medium using 50% ammonium sulfate precipitation followed by Protein A affinity chromatography. The purity of the IgG fraction was determined by a stained SDS-PAGE (FIG. 4A) and Western Blot analysis (FIG. 4B) using rabbit anti-FCS.

Figure 5:
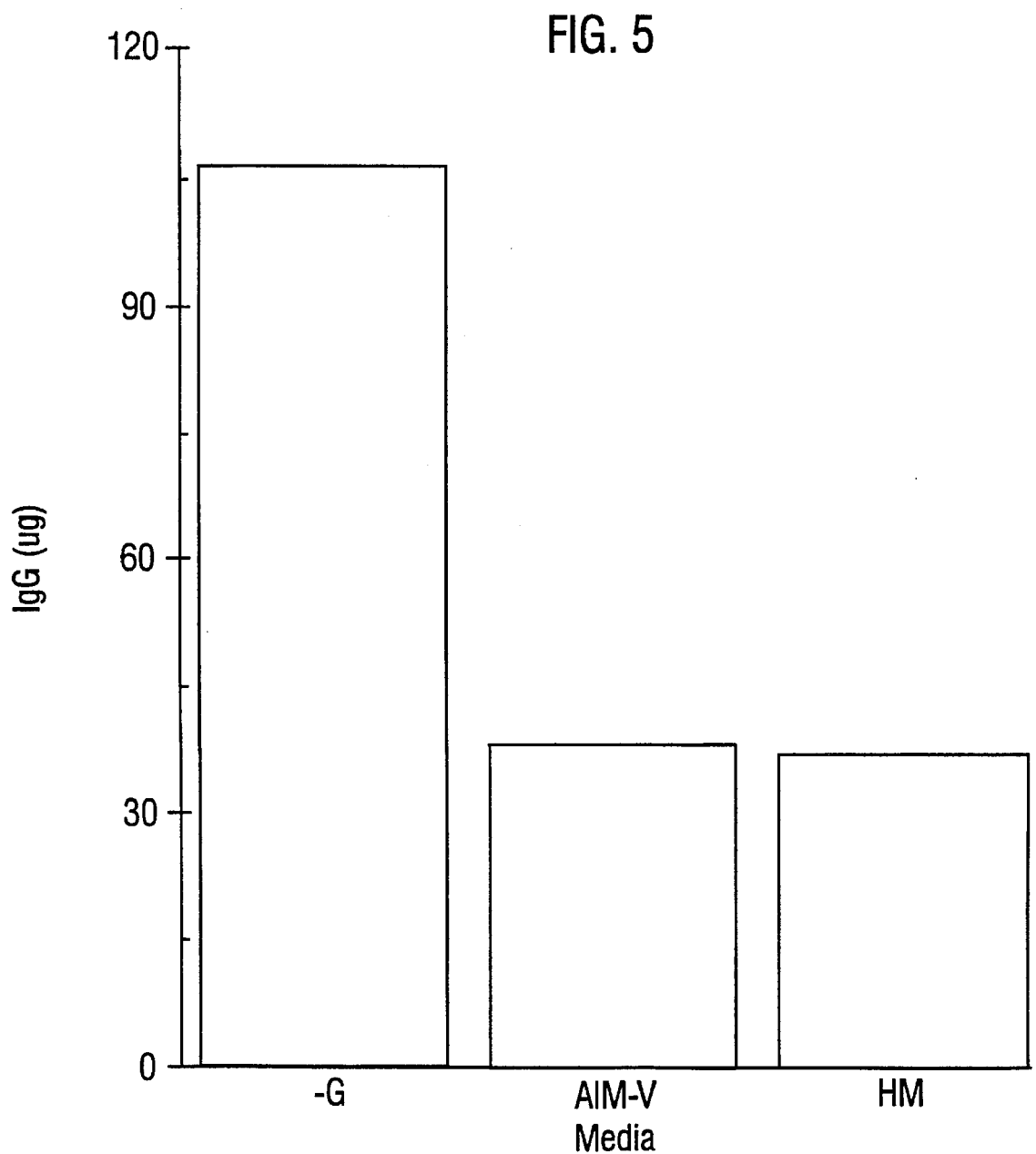
FIG. 5 Chimeric IgG yield from TVE-1 cells in –GFCS and other media. Chimeric IgG yields from 40 ml of TVE-1 cell culture supernatants after 3 days culture in –GFCS and other media were examined. Chimeric IgG was purified as described in Example 3 and the $OD_{280}$ value was determined by ultra violet spectrophotometry. TVE-1 cells cultured in –GFCS produced approximately 2.8 times more IgG than TVE-1 cells cultured in either AIM-V or HM.

Only the bands from the monoclonal IgG were visible in the lane of the purified TVE-1 antibody fraction. The protein bands of IgG or its H and L chains can be detected by direct staining of an SDS-PAGE gel or by Western Blot analysis. On the other hand, faint bands (equivalent to bovine albumin) were detected even in FCS diluted 1:10,000. This indicates that the possible contamination of TVE-1 IgG by –GFCS is less than 1:10,000. FIG. 5 demonstrates the difference in IgG yield from the TVE-1 cell line grown in –G and the other two media; IgG content was determined by $OD_{280}$. Cells cultured in –G produced about 2.8 fold more TVE-1 IgG than did those cultured in the other two serum-free media.

EXAMPLE 7

Comparison of Cell Growth and Antibody Production in "Cell-Keeping" vs "Cell-Transferring" Cultures Further studies were done to compare the cell growth, viability, and IgG yield from the customary procedures of TVE-1 antibody production (Hasting et al., 1992) with that of the newly developed –GFCS culture method. The studies were performed as follows: TVE-1 cells cultured in –G medium were collected, and $2\times10^5/5$ ml TVE-1 cells per T25 were dispensed into 32 flasks. After 7 days culture, the 32 flasks were divided randomly into 4 groups. In Group I, designated "cell-keeping", only the medium was changed. Cells from the other 24 flasks were collected, washed and centrifuged three times, dispensed to 24 new flasks divided into Groups II, III, IV, and then cultured in –GFCS medium for 2 days (Group I and Group II); for 4 days (Group III); or for 7 days (Group IV). Comparisons were made of the cell growth and the IgG yields in the "cell-keeping" and "cell-transferring" groups.

Figure 6A:
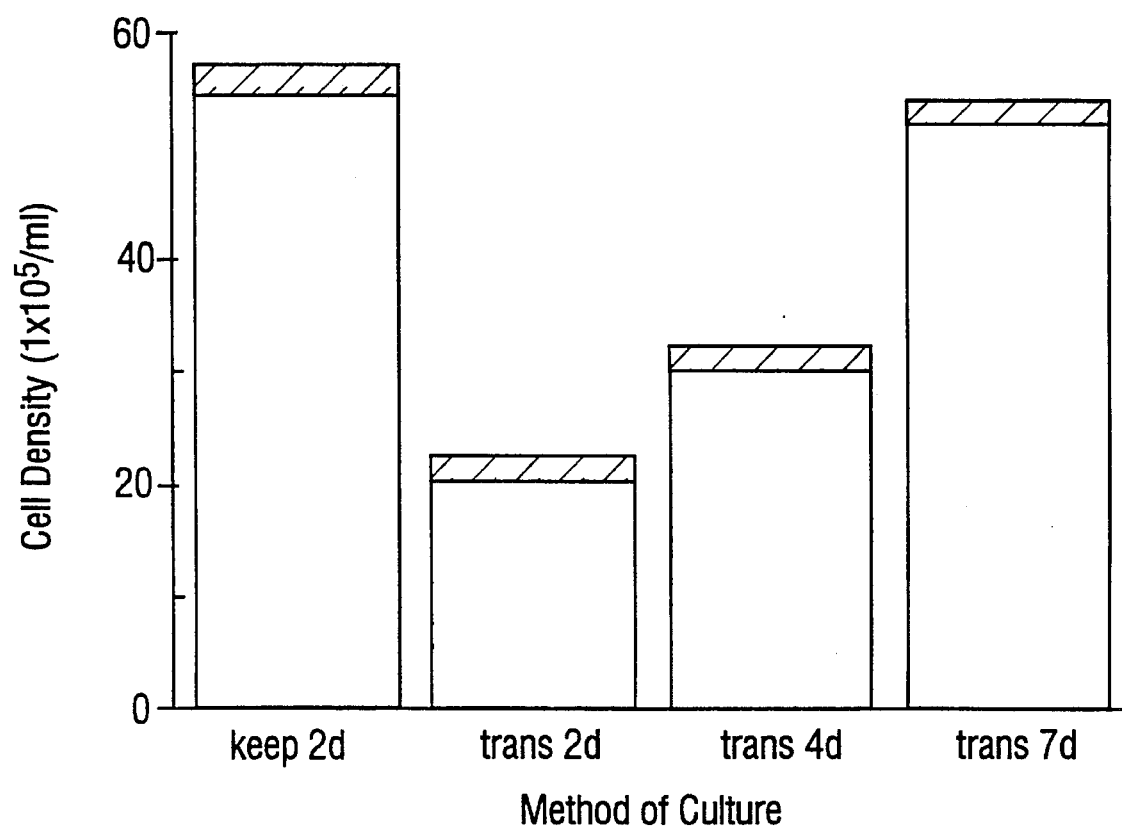
FIG. 6A Cell density of TVE-1 cells grown by "cell-keeping" vs "cell-transferring" culture. Column 1 represents TVE-1 cell growth when the "cell-keeping" procedure was followed and cells were kept in the same flask of –GFCS medium for two days. Columns 2, 3, and 4 represent cell growth when the "cell-transferring" procedure was followed. In the "cell-transferring" procedure, the cultured cells were collected and washed three times by centrifugation, then transferred to a new flask with –GFCS medium and cultured for 2, 4, and 7 days respectively. The starting cell count was $2 \times 10^5/5$ ml/flask. After about 7 days, the cell density in the "cell-transferring" culture approached the same level as that in the "cell-keeping" culture.
Figure 6B:
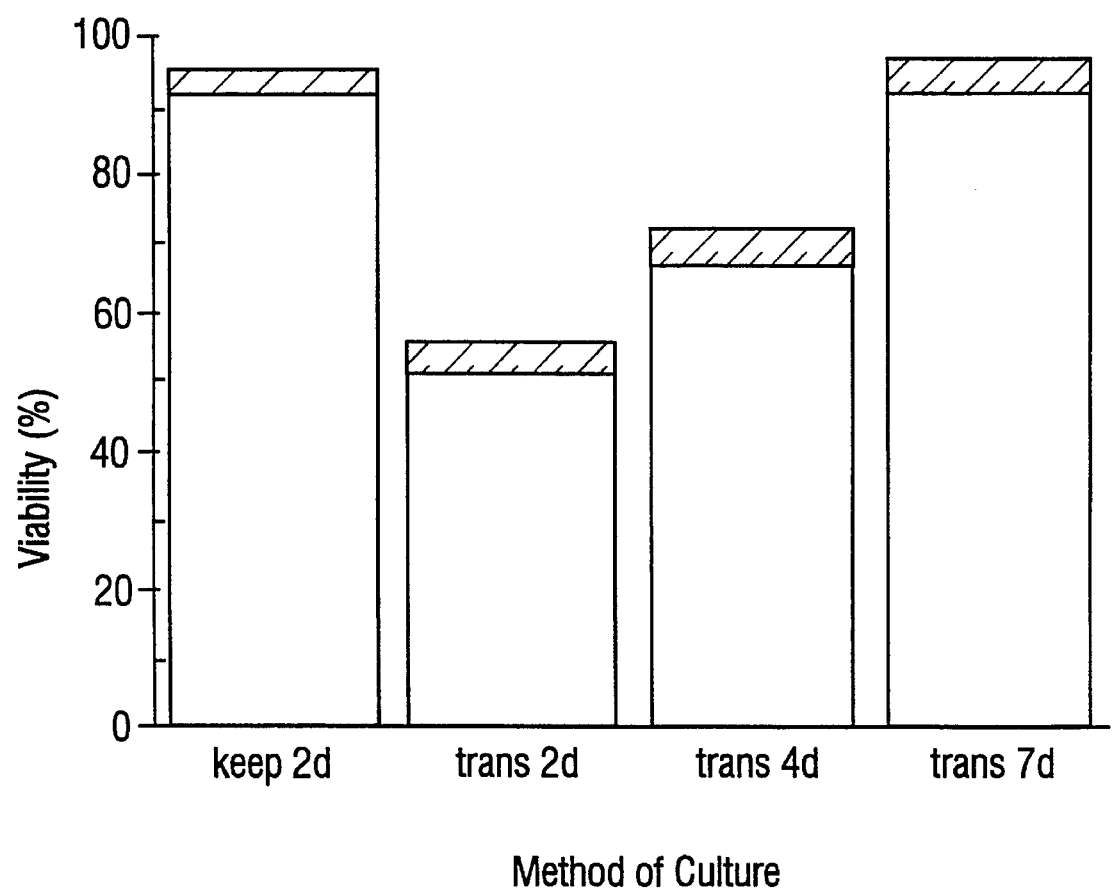
FIG. 6B represents the cell viability (%) from the cultures as described in FIG. 6A. Again, after about 7 days, the viability in the "cell-transferring" culture reached the same level as that in the "cell-keeping" culture.
Figure 7:
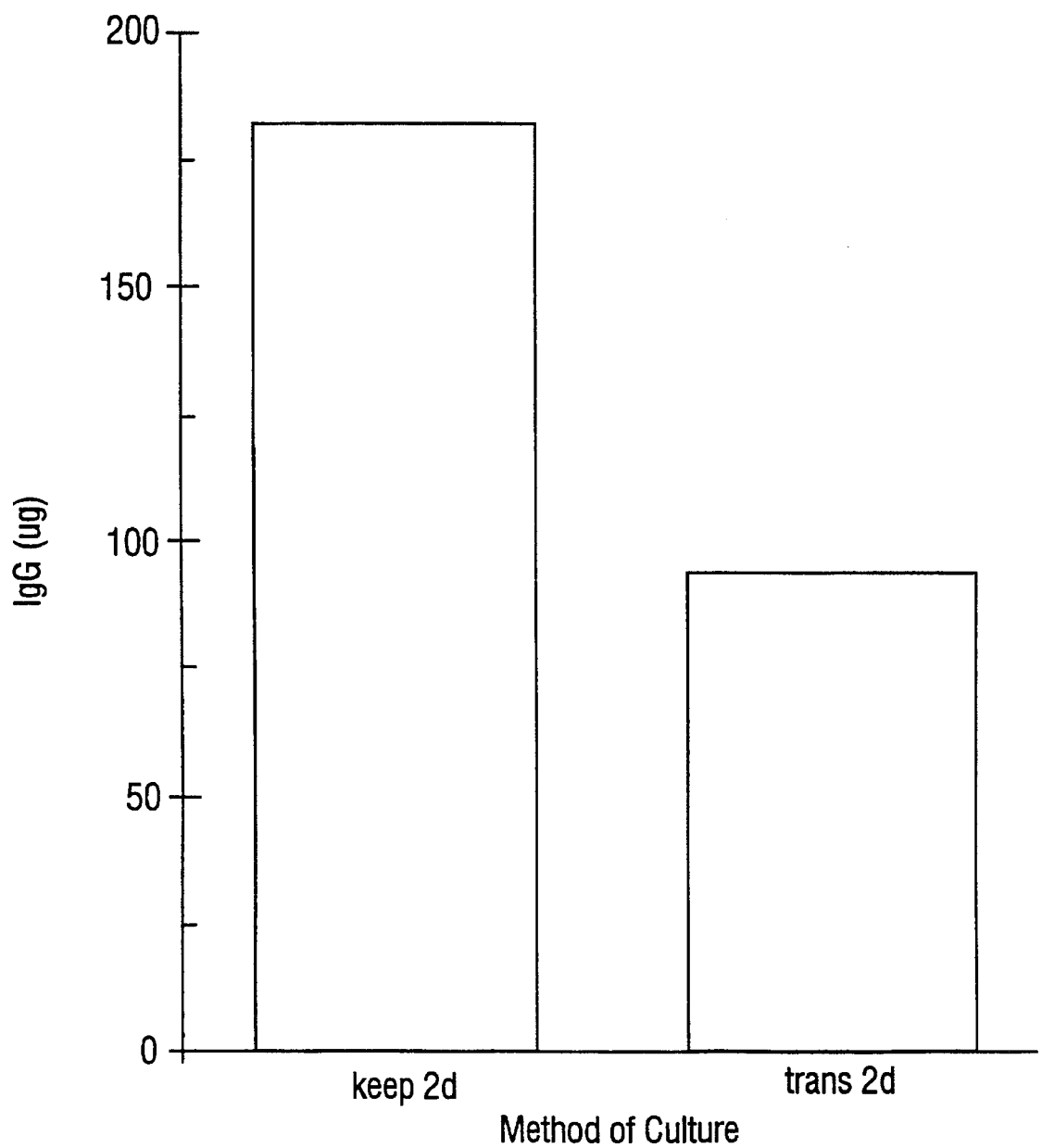
FIG. 7 Chimeric IgG yield from the "cell-keeping" culture vs. the "cell-transferring" culture. Chimeric IgG yields (μg) from the supernatants of the cultures as described in FIG. 6A were determined after purification of the IgG fraction. According to the $OD_{280}$ values, the IgG yield from the "cell-keeping" culture was approximately twice that from the "cell-transferring" culture during the same two-day period.

The cell density (FIG. 6A) and viability (FIG. 6B) in the 2 day "cell-keeping" culture, and from the 2, 4, and 7 days "cell-transferring" culture were compared. Only after 7 days did the cell density and viability in the "cell-transferring" culture reach the level of the 2 day "cell-keeping" culture. FIG. 7 demonstrates that the IgG yields from the "cell-keeping" culture (18.1 μg/ml) were almost twice as much as the "cell-transferring" culture (9.3 μg/ml) in the same 2-day period.

While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references are specifically incorporated herein by reference in pertinent part for the purposes indicated.

Akerstrom et al. (1985) Protein G: A powerful tool for binding and detection of monoclonal and polyclonal antibodies. J. Immunol. 135:2589.

Barnes, D. (1987) Serum-free animal cell culture. Biotechniques 5:534.

Barnes, D. and Sato, G. (1980) Methods for growth of cultured cells in serum-free medium. Ann. Biochem. 102:255.

Bjorck, L. and Kronvall, G. (1984) Purification and some properties of Streptococcal protein G, a novel IgG-binding reagent. J. Immunol. 133:969.

Boyle, M. D. P. and Reis, K. J. (1987) Bacterial Fc receptors. Biotechnol. 5:697.

Fahnstock et al. (1986) Gene for an immunoglobulin-binding protein from a group G Streptococcus. J. Bacteriol. 167:870.

Federspiel et al. (1991) Hybridoma antibody production in vitro in type II serum-free medium using Nutridoma-SP supplements. Comparisons with in vivo methods. J. Immunol. Methods 145:213.

Freshney, R. I. (1987) Measurement of cytotoxicity and viability. In: R. I. Freshney (Ed.), Culture of animal cells: Manual of basic technique. A. R. Liss, New York, p. 245.

Glassy et al. (1988) Serum-free media in hybridoma culture and monoclonal antibody production. Biotechnol. Bioeng. 32:1015.

Goding, J. W. (1978) Use of staphylococcal protein A as an immunological reagent. J. Immunol. Methods 20:241.

Guss et al. (1986) Structure of the IgG-binding regions of streptococcal protein G. EMBO J. 5:1567.

Hastings et al. (1992) Production and characterization of a murine/human chimeric anti-idiotype antibody that mimics ganglioside. Cancer Res. 52:1681.

Jayme, D. W. and Blackman, K. E. (1985) Culture media for propagation of mammalian cells, viruses, and other biologicals. Adv. Biotechnol. Proc. 5:1.

Lew et al. (1991) Recombinant fusion protein of protein A and protein G with glutathione S-transferase as reporter molecules. J. Immunol. Methods 136:211.

Mariani et al. (1991) Commercial serum-free media: hybridoma growth and monoclonal antibody production. J. Immunol. Methods 145:175.

Nygren et al. (1988) Analysis and use of the serum albumin binding domains of streptococcal protein G. J. Mol. Recognition 1:89.

Saito et al. (1990) Murine monoclonal anti-idiotype antibody (α) as a probe to detect human monoclonal antibody bound to human tumor tissues. J. Immunol. Methods 134:121.

Schneider, Y-J. (1989) Optimization of hybridoma cell growth and monoclonal antibody secretion in a chemically defined, serum- and protein-free culture medium. J. Immunol. Methods 116:65.

Schneider, Y-J. and Lavoix, A. (1990) Monoclonal antibody production in semi-continuous serum- and protein-free culture. J. Immunol. Methods 129:251.

What is claimed is:

1. A serum preparation comprising an animal serum containing less than about 1 µg/ml of IgG antibody.

2. The serum preparation of claim 1 wherein the animal serum is bovine serum.

3. The serum preparation of claim 2 wherein the bovine serum is fetal calf serum.

4. The serum preparation of claim 1 wherein the serum preparation contains less than about 0.4 µg/ml IgG.

5. The serum preparation of claim 4 wherein the serum preparation contains less than about 0.01 µg/ml IgG.

6. The serum preparation of claim 1 wherein said serum preparation is prepared by contacting the serum with protein A or protein G to deplete said serum of IgG.

7. An animal serum preparation containing less than about 0.4 µg/ml of IgG produced by the process which comprises the following steps:
(a) contacting a volume of animal serum with protein G or protein A affixed to a solid substrate; and
(b) collecting said animal serum preparation.

8. The animal serum preparation of claim 7 wherein the animal serum is fetal calf serum.

9. The animal serum preparation of claim 8 wherein the preparation is essentially free of endotoxin.

10. The animal serum preparation of claim 7 wherein the solid substrate is acrylic, agarose or SEPHAROSE.

11. The animal serum preparation of claim 10 wherein the SEPHAROSE is SEPHAROSE 4B fast flow.

12. A cell culture media for the culture of an antibody producing cell line comprising a basal culture media and less than about 5% of a serum supplement, said serum supplement containing less than about 0.4 µg/ml IgG.

13. The cell culture media of claim 12 wherein the serum supplement contains less than about 0.01 µg/ml IgG.

14. The cell culture media of claim 12 wherein the serum supplement is a fetal calf serum supplement.

15. The cell culture media of claim 12 wherein said antibody producing cell line produces IgG antibody.

16. The cell culture media of claim 12 wherein the basal culture media is RPMI 1640.

17. The cell culture media of claim 12 wherein the antibody producing cell line is TVE-1.

18. The cell culture media of claim 12 wherein said serum supplement is prepared by contacting the serum with protein A or protein G to deplete said serum of IgG.

19. A method of culturing hybridoma cells comprising:
(a) preparing an IgG depleted animal serum by contacting said animal serum with protein G or protein A and collecting said serum, wherein said IgG depleted animal serum contains less than about 1 µg/ml IgG;
(b) adding said IgG depleted animal serum to a culture medium; and
(c) culturing an antibody producing cell line in said culture medium.

20. The method of claim 19 wherein said protein A or protein G is fixed to a solid substrate.

21. The method of claim 20 wherein said solid substrate is acrylic, agarose or SEPHAROSE.

22. The method of claim 21 wherein said SEPHAROSE is SEPHAROSE 4B fast flow.

23. The method of claim 19 wherein said animal serum is bovine, goat, horse, pig or human serum.

24. The method of claim 23 wherein said animal serum is bovine serum.

25. The method of claim 24 wherein said bovine serum is fetal calf serum.

26. The method of claim 19 wherein said IgG depleted serum contains less than about 0.4 µg/ml IgG.

27. The method of claim 19 wherein said IgG depleted serum contains less than about 0.01 µg/ml IgG.

28. A method of preparing a monoclonal antibody comprising:

(a) preparing an IgG depleted animal serum by contacting said serum with protein A or protein G and separating said protein A or protein G from said animal serum, wherein said IgG depleted animal serum contains less than about 1 µg/ml IgG;

(b) collecting said IgG depleted animal serum to a culture medium;

(c) culturing a cell line capable of producing said monoclonal antibody in said culture medium; and (d) adding said monoclonal antibody.

29. The method of claim 28 wherein said monoclonal antibody is an IgG monoclonal antibody.

30. The method of claim 28 wherein said cell line is an antibody producing cell line selected from the group consisting of hybridoma, transfectoma, B-lymphoblast and myeloma.

31. The method of claim 28 wherein said cell line is a myeloma cell line.

32. The method of claim 31 wherein said myeloma cell line is a mouse myeloma cell line.

33. The method of claim 28 wherein said IgG depleted serum comprises less than about 5% of said culture medium by volume.

34. The method of claim 33 wherein said IgG depleted serum comprises about 1–2% of said culture medium by volume.

* * * * *

UNITED STATES PATENT AND TRADEMARK OFFICE
CERTIFICATE OF CORRECTION

PATENT NO. : 5,593,822
DATED : January 14, 1997
INVENTOR(S) : Zeng et al.

It is certified that error appears in the above-identified patent and that said Letters Patent is hereby corrected as shown below:

In claim 28, column 15, line 18, please delete "collecting" and insert -- adding -- therefor.

In claim 28, column 16, line 1, please delete "adding" and insert -- collecting -- therefor.

Signed and Sealed this

Eighth Day of April, 1997

Attest:

BRUCE LEHMAN

*Attesting Officer*　　　*Commissioner of Patents and Trademarks*